(12) United States Patent
Nakamura et al.

(10) Patent No.: US 9,052,286 B2
(45) Date of Patent: Jun. 9, 2015

(54) FLUORESCENCE ENDOSCOPE APPARATUS

(71) Applicant: OLYMPUS CORPORATION, Tokyo (JP)

(72) Inventors: Kazunari Nakamura, Tokyo (JP); Motohiro Mitamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 221 days.

(21) Appl. No.: 13/897,516

(22) Filed: May 20, 2013

(65) Prior Publication Data

US 2013/0250079 A1    Sep. 26, 2013

Related U.S. Application Data

(63) Continuation of application No. PCT/JP2011/073476, filed on Oct. 13, 2011.

(30) Foreign Application Priority Data

Nov. 26, 2010 (JP) ................................ 2010-263990

(51) Int. Cl.
*A61B 1/00* (2006.01)
*G01N 21/64* (2006.01)
(Continued)

(52) U.S. Cl.
CPC ............ *G01N 21/64* (2013.01); *A61B 1/00009* (2013.01); *A61B 1/043* (2013.01);
(Continued)

(58) Field of Classification Search
CPC ..... A61B 1/043; A61B 5/0057; A61B 5/0071
USPC .......................................................... 348/65
See application file for complete search history.

(56) References Cited

U.S. PATENT DOCUMENTS

2004/0257438 A1* 12/2004 Doguchi et al. ................ 348/65

FOREIGN PATENT DOCUMENTS

| JP | 10-123453 A | 5/1998 |
|----|----|----|
| JP | 10-201707 A | 8/1998 |

(Continued)

OTHER PUBLICATIONS

International Search Report dated Nov. 15, 2011 issued in PCT/JP2011/073476.

*Primary Examiner* — Sath V Perungavoor
*Assistant Examiner* — Jeffery Williams
(74) *Attorney, Agent, or Firm* — Scully, Scott, Murphy & Presser, P.C.

(57) ABSTRACT

A fluorescence endoscope apparatus includes an illuminating portion radiating excitation light and illumination light onto an imaging subject; a fluorescence imaging portion acquiring a fluorescence image by capturing fluorescence emitted at the imaging subject due to the irradiation with the excitation light; a storage portion storing the fluorescence image; a return-light imaging portion acquiring a return-light image by capturing return light returning from the imaging subject due to the irradiation with the illumination light; an image-information extracting portion extracting, from the return-light image, image information that expresses the intensity of the illumination light; a number-of-integrated-images setting portion setting a number of integrated images so that the number is decreased with an increase in the intensity of the illumination light, based on the image information; and an average-image generating portion generating an average image by averaging the stored fluorescence images in a number corresponding to the set number of integrated images.

9 Claims, 4 Drawing Sheets

(51) Int. Cl.
 *A61B 1/04* (2006.01)
 *G02B 23/24* (2006.01)
 *H04N 5/225* (2006.01)
(52) U.S. Cl.
 CPC .......... *G02B23/2461* (2013.01); *H04N 5/2256* (2013.01); *G02B 23/2484* (2013.01); *H04N 2005/2255* (2013.01)

(56) References Cited

FOREIGN PATENT DOCUMENTS

| | | |
|---|---|---|
| JP | 2003-164416 A | 6/2003 |
| JP | 2005-261974 A | 9/2005 |
| JP | 2008-310130 A | 12/2008 |

* cited by examiner

FLUORESCENCE ENDOSCOPE APPARATUS

CROSS-REFERENCE TO RELATED APPLICATIONS

This is a continuation of International Application PCT/JP2011/073476, with an international filing date of Oct. 13, 2011, which is hereby incorporated by reference herein in its entirety. This application is based on Japanese Patent Application No. 2010-263990, the contents of which are incorporated herein by reference.

TECHNICAL FIELD

The present invention relates to a fluorescence endoscope apparatus.

BACKGROUND ART

In the related art, there is a known fluorescence endoscope apparatus with which a fluorescence image and a reflected-light image of an observation subject are acquired by irradiating light in a wavelength band for exciting a fluorescent substance and light in a wavelength band for normal observation while switching between them by means of a rotating filter, and both images are observed with appropriate brightnesses (for example, see Patent Literature 1). With this fluorescence endoscope apparatus, the aperture and exposure time for a liquid crystal are changed depending on whether or not fluorescence observation is performed; image data that is imaged and signal converted by a CCD is multiplied by a preset coefficient; this is added to image data accumulated up to one frame immediately before it, which is stored in a frame memory; and the data is stored in the frame memory and is also output.

CITATION LIST

Patent Literature

{PTL 1} Japanese Unexamined Patent Application, Publication No. 2005-261974

SUMMARY OF INVENTION

An aspect of the present invention is a fluorescence endoscope apparatus including an illuminating portion that radiates excitation light and illumination light onto an imaging subject; a fluorescence imaging portion that acquires a fluorescence image by capturing fluorescence emitted at the imaging subject due to the irradiation with the excitation light from the illuminating portion; a storage portion that stores the fluorescence image acquired by the fluorescence imaging portion; a return-light imaging portion that acquires a return-light image by capturing return light returning from the imaging subject due to the irradiation with the illumination light from the illuminating portion; an image-information extracting portion that extracts, from the return-light image acquired by the return-light imaging portion, image information that expresses the intensity of the illumination light radiated onto the imaging subject; a number-of-integrated-images setting portion that sets a number of integrated images so that the number is decreased with an increase in the intensity of the illumination light, based on the image information extracted by the image-information extracting portion; and an average-image generating portion that generates an average image by averaging the fluorescence images, stored in the storage portion, in a number corresponding to the number of integrated images set by the number-of-integrated-images setting portion.

DESCRIPTION OF EMBODIMENTS

A fluorescence endoscope apparatus 1 according to a first embodiment of the present invention will be described below with reference to the drawings.

Figure 1:
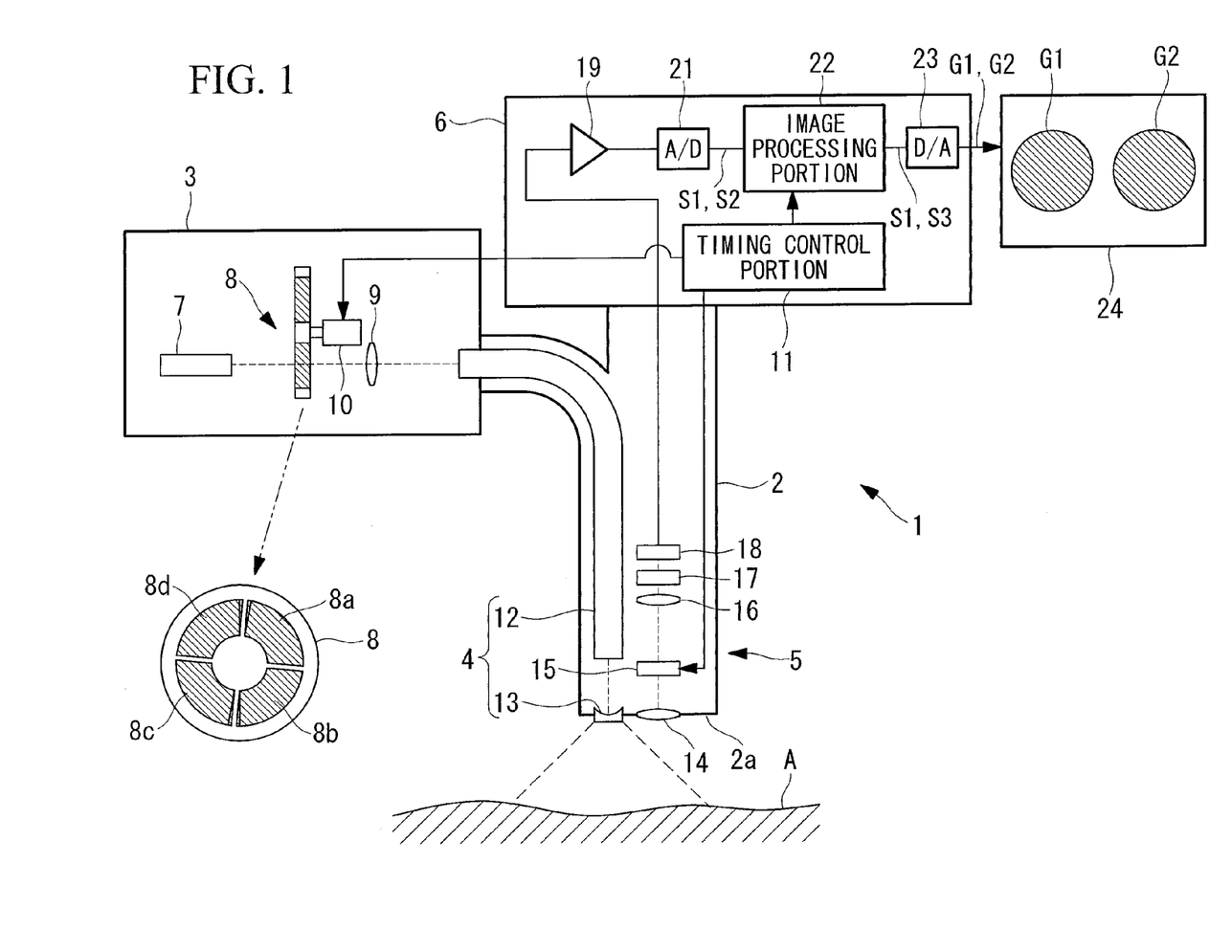
FIG. 1 is an overall configuration diagram showing a fluorescence endoscope apparatus according to a first embodiment of the present invention.

As shown in FIG. 1, the fluorescence endoscope apparatus according to this embodiment is provided with a long, thin inserted portion 2 that is inserted into a body; a light source (illuminating portion) 3; an illuminating unit (illuminating portion) 4 that radiates excitation light and illumination light from the light source 3 onto an imaging subject A from the distal end of the inserted portion 2; an imaging unit 5 that is provided at the distal end of the inserted portion 2 and that acquires image information about biological tissue, that is, the imaging subject A; a processor 6 that is disposed at the base end of the inserted portion 2 and that processes the image information acquired by the imaging unit 5; and a monitor 24 that displays an image G processed by the processor 6.

The light source 3 is provided with a xenon lamp 7 that emits light in a wavelength band (400 to 740 nm) including the excitation light and the illumination light; a filter turret 8 that is provided in an illumination optical path of the xenon lamp 7 and that includes a plurality of filters 8a to 8d for restricting the transmitted wavelength; and a coupling lens 9 that focuses the excitation light and the illumination light extracted by the individual filters 8a to 8d. The filter turret 8 is rotationally driven by a motor 10, and the motor 10 is controlled at a certain rotation speed by a timing control portion 11, described later.

The filter turret 8 is provided with the four filters 8a to 8d, that is, an R-filter 8a, a G-filter 8b, a B-filter 8c, and an IR-filter 8d, arranged in the circumferential direction. By being rotated about a rotation shaft at the center, this filter turret 8 places the R-filter 8a, the G-filter 8b, or the B-filter 8c in the optical path during return-light observation, and places the IR-filter 8d in the optical path during fluorescence observation.

Figure 3:
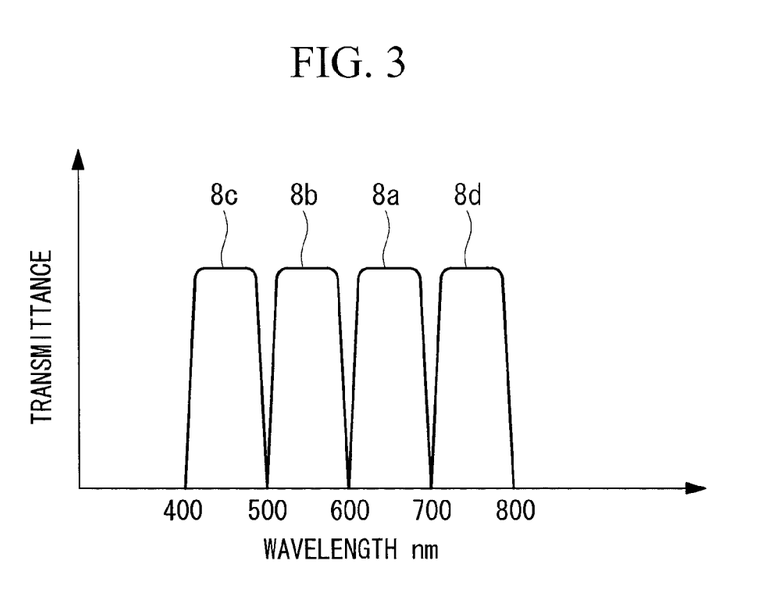
FIG. 3 is a diagram showing the spectral transmission characteristic of a filter turret provided in the fluorescence endoscope apparatus in FIG. 1.

FIG. 3 shows the transmission characteristics of the R-filter 8a, the G-filter 8b, the B-filter 8c, and the IR-filter 8d. The R-filter 8a, the G-filter 8b, and the B-filter 8c possess characteristics whereby they transmit red, green, and blue wavelength components, respectively, and the IR-filter 8d possesses a characteristic whereby they transmit an excitation-light component.

The illuminating unit 4 is provided with a light-guide fiber 12 that is disposed along nearly the entire length of the inserted portion 2 in the longitudinal direction thereof and that guides the excitation light and the illumination light focused by the coupling lens 9; and an illumination optical system 13 that is provided at the distal end of the inserted portion 2, that spreads the excitation light and the illumination light guided thereto by the light-guide fiber 12, and that radiates the excitation light and the illumination light onto the imaging subject A facing a distal-end surface 2a of the inserted portion 2.

The imaging unit 5 is provided with an objective lens 14 that collects light returning from a predetermined observation area of the imaging subject A; a liquid-crystal aperture portion 15 that serves as an aperture means for limiting the light level of return light collected by the objective lens 14; a light focusing lens 16 that focuses the return light limited by the liquid-crystal aperture 15; an excitation-light cut filter 17 that, of the light focused by the light focusing lens 16, blocks light having a wavelength equal to or lower than the excitation wavelength and allows fluorescence components and return-light components to pass therethrough; and an imaging device 18, such as a CCD, that captures the fluorescence and the return light that have passed through the excitation-light cut filter 17. The liquid-crystal aperture portion 15 possesses the property that the liquid-crystal aperture portion 15 does not allow light to pass therethrough when a voltage is applied thereto and allows light to pass therethrough when voltage is not applied thereto.

The processor 6 includes a preamplifier 19 that amplifies image signals that have been photoelectrically converted by the imaging device 18 and an A/D converting portion 21. Image signals that have been A/D converted by the A/D converting portion 21 are input to an image processing portion 22 in the form of return-light image information S1 and fluorescence image information S2 and are subjected to image processing at the image processing portion 22. The return-light image information S1 and average fluorescence image information S3 that have been subjected to the image processing at the image processing portion 22 are D/A converted at a D/A converting portion 23 and are output to the monitor 24.

In addition, the processor 6 is provided with the timing control portion 11 that controls the filter turret 8, data buffers 25, and the liquid-crystal aperture portion 15. The timing control portion 11 controls, in synchronization, the rotation of the filter turret 8, data allocation to the data buffers, and the aperture level of the liquid-crystal aperture portion. Specifically, the control is performed so that the liquid-crystal aperture portion is closed to reduce the light level when observing the return light, whose light level is high, and the liquid-crystal aperture portion is opened when observing the fluorescence, whose light level is low, so that as much fluorescence as possible can be received.

Figure 4:
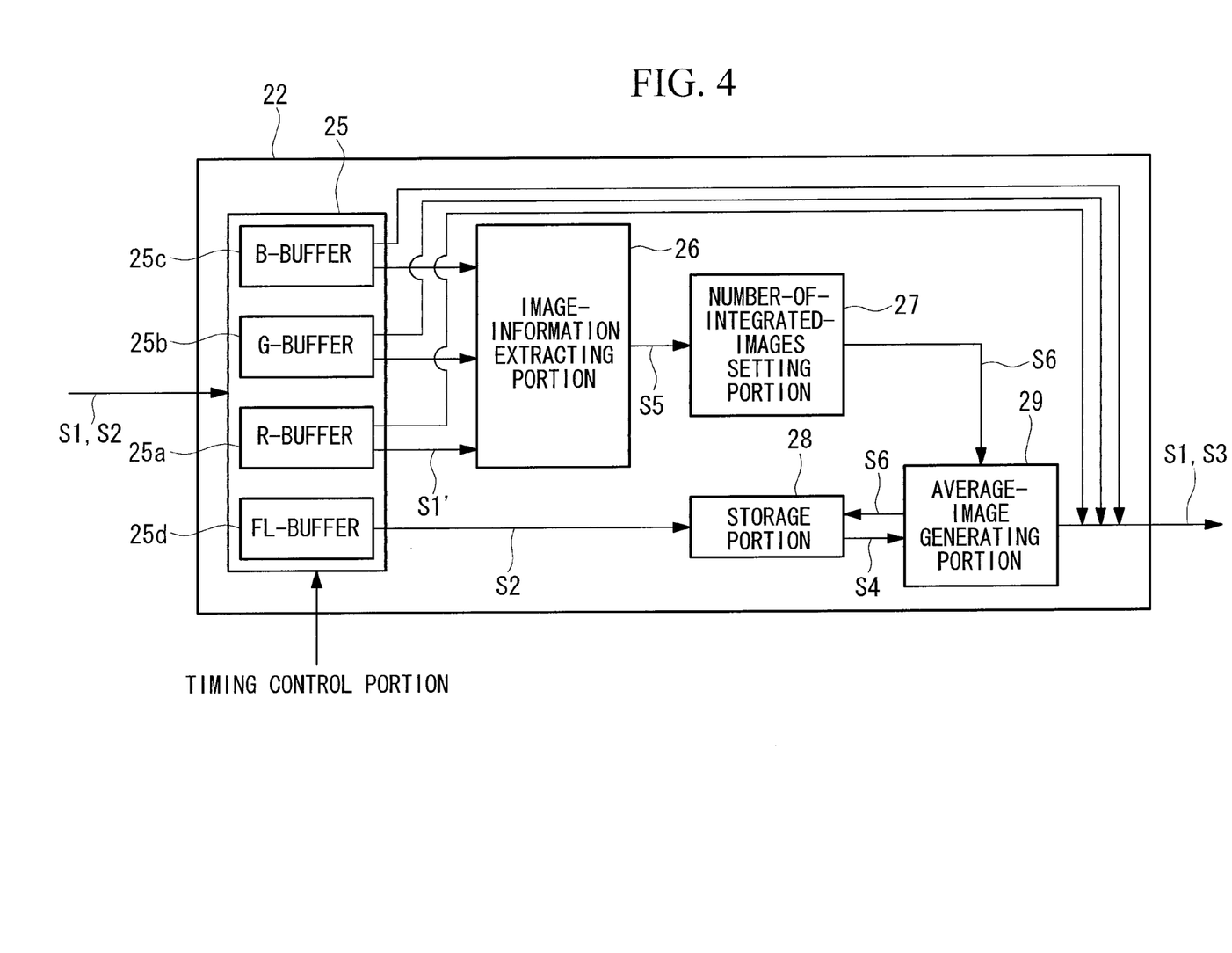
FIG. 4 is a diagram showing an image processing portion of the fluorescence endoscope apparatus in FIG. 1.

As shown in FIG. 4, the image processing portion 22 is provided with the data buffers 25 (hereinafter, referred to as an R-buffer 25a, a G-buffer 25b, a B-buffer 25c, and an FL-buffer 25d) that temporarily store the image information S1 and S2 that have been A/D converted; an image-information extracting portion 26 that extracts an average gradation value S5 of the return-light image information S1 that is output from the R-buffer 25a, the G-buffer 25b, and the B-buffer 25c; a number-of-integrated-images setting portion 27 that sets a number S6 of integrated images for the fluorescence images based on the average gradation value S5 extracted by the image-information extracting portion 26; a storage portion 28 that sequentially stores the fluorescence image information S2 that is output from the FL-buffer; and an average-image generating portion 29 that generates the average fluorescence image information S3 by averaging the fluorescence image information S4, stored in the storage portion 28, in an amount corresponding to the number S6 of integrated images.

In addition, the image-information extracting portion 26 extracts the average gradation value S5 by selecting the return-light image information S1 that is output from one of the R-buffer 25a, the G-buffer 25b, and the B-buffer 25c. In this embodiment, the image-information extracting portion 26 calculates the average gradation value S5 by using, for example, return-light image information S1' that is output from the R-buffer 25a.

Figure 2:
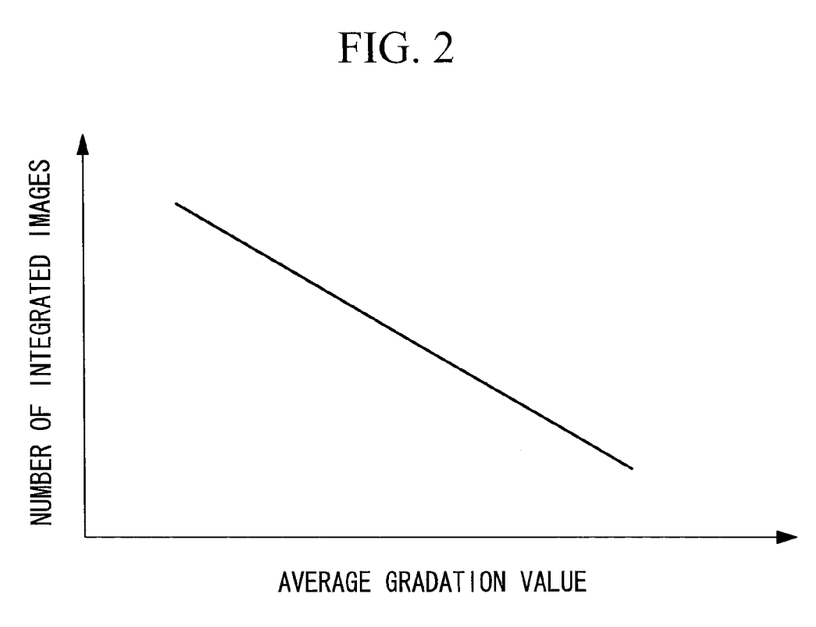
FIG. 2 is a diagram showing an example monotonically increasing function for setting a number of integrated images in the fluorescence endoscope apparatus in FIG. 1, wherein the number of integrated images is decreased with an increase in an average gradation value.

Here, as shown in FIG. 2, the number-of-integrated-images setting portion 27 in this embodiment stores a function with which the number S6 of integrated images is set so that the number is decreased with an increase in the average gradation value S5 calculated at the image-information extracting portion 26.

This function is obtained in advance from the relationship between the average gradation value S5 of the return-light image obtained by capturing an image of a standard specimen or the like and the number S6 of integrated images with which the average fluorescence image is obtained with high precision. Because the intensity of the excitation light increases with an increase in the brightness of the return-light image, in order to reduce image blurring caused by using a large number S6 of integrated images, a monotonically decreasing function is employed, with which the number S6 of integrated images is decreased with an increase in the average gradation value S5, as shown in FIG. 2.

In addition, the storage portion 28 is a ring buffer that stores the fluorescence image information S2 input from the FL-buffer in time series. Then, in response to a request from the average-image generating portion 29, the storage portion 28 outputs the fluorescence image information S4 to the average-image generating portion 29 in an amount corresponding to the number S6 of integrated images, based on the number S6 of integrated images generated by the number-of-integrated-images setting portion 27.

The average-image generating portion 29 transmits the number S6 of integrated images set by the number-of-integrated-images setting portion 27 to the storage portion 28, and, of the fluorescence image information stored in the storage portion 28, requests the fluorescence image information S4 to be output in an amount corresponding to the number S6 of integrated images by backtracking from the most recent information. Then, at the average-image generation portion 29, the fluorescence image information S4 in the amount corresponding to the number S6 of integrated images, which has been obtained from the storage portion 28 in response to the request, is integrated and is subsequently divided by the number S6 of integrated images, thus generating the average fluorescence image information S3.

The operation of the thus-configured fluorescence endoscope apparatus 1 according to this embodiment will be described below.

To observe biological tissue in the body, that is, the imaging subject A, by using the fluorescence endoscope apparatus 1 according to this embodiment, the inserted portion 2 is inserted into the body, and the distal end surface 2a of the inserted portion 2 is disposed facing the imaging subject A. Then, the light source 3 is activated.

The light emitted from the light source 3 forms the excitation light and the illumination light by passing through the individual filters 8a to 8d of the filter turret 8. Specifically, because the individual filters 8a to 8d possess the transmittance characteristics shown in FIG. 3, red, green, and blue illumination light is formed by passing through the R-filter 8a, the G-filter 8b, and the B-filter 8c, and excitation light in the infrared region is formed by passing through the IR-filter 8d. The light that is turned into the illumination light or the excitation light is subsequently made to enter the light-guide fiber 12 by the coupling lens 9. The excitation light and the illumination light that have reached the distal end of the inserted portion 2 by being guided through the light-guide fiber 12 are radiated onto the imaging subject A by being spread out by the illumination optical system 13 at the distal end surface 2a of the inserted portion.

When the excitation light is radiated onto the imaging subject A, fluorescent substances contained in the imaging subject A are excited, thus emitting fluorescence. On the other hand, when the illumination light is radiated onto the imaging subject A, the radiated illumination light is reflected at the surface of the imaging subject A. The fluorescence and return light of the illumination light return to the distal end surface 2a of the inserted portion 2 from the imaging subject A to be collected by the objective lens 14.

The fluorescence and visible light collected by the objective lens 14 are focused by the light focusing lens 16 after being limited by the liquid-crystal aperture portion 15, and are captured by the imaging device 18 via the excitation-light cut filter 17.

Therefore, the imaging device 18 receives one of red, green, blue visible light, and infrared fluorescence, depending on the position of the filter turret 8. The imaging device 18 is driven in synchronization with the rotation of the filter turret 8 by an imaging-device driving circuit (not shown), and acquires electrical signals that individually represent a return-light image and a fluorescence image.

The electrical signals representing the return-light image and the fluorescence image acquired by the imaging device 18 are input to and amplified by the preamplifier 19 in the processor 6, and the image signals are subsequently input to the A/D converting portion 21, thus being converted from analog signals to digital signals.

The digital image signals are input to the R-buffer 25a, the G-buffer 25b, the B-buffer 25c or the FL-buffer 25d in the image processing portion 22 depending on the types thereof. Based on control signals from the timing control portion 11, the signals are switched so that the data buffers 25 receive inputs thereof at the R-buffer 25a when the R-filter 8a of the filter turret 8 is inserted, at the G-buffer 25b when the G-filter 8b is inserted, at the B-buffer 25c when the B-filter 8c is inserted, and at the FL-buffer 25d when the IR-filter 8d is inserted.

The return-light image information S1 input to the R-buffer 25a, the G-buffer 25b, or the B-buffer 25c is transmitted to the D/A converting portion 23 and the image-information extracting portion 26. At the image-information extracting portion 26, by using the return-light image information S1' output from the R-buffer 25a, gradation values of all pixels in the return-light image are summed and averaged, and thus, the average gradation value S5 is calculated and output to the number-of-integrated-images setting portion 27.

At the number-of-integrated-images setting portion 27, the number S6 of integrated images is set by applying the average gradation value S5 input from the image-information extracting portion 26 to the function that is stored in advance and is then output to the storage portion 28.

The fluorescence image information S2 input to the FL-buffer 25d are stored in the storage portion 28 in time series. Then, the fluorescence image information S4 stored in the storage portion 28 is output to the average-image generating portion 29 in the amount corresponding to the number S6 of integrated images input from the number-of-integrated-images setting portion 27.

At the average-image generating portion 29, the fluorescence image information S4 is input from the storage portion 28 in the amount corresponding to the number S6 of integrated images, and the average fluorescence image information S3 obtained by averaging that fluorescence image information S4 is output to the D/A converting portion 23.

Then, at the D/A converting portion 23, the generated average fluorescence image information S3 and the return-light image information S1 output from the R-buffer 25a, the G-buffer 25b, and B-buffer 25c are input and D/A converted, and a return-light image G1 and an average fluorescence image G2 are output to the monitor 24.

As shown in FIG. 1, when displaying the return-light image G1 and the average fluorescence image G2 on the monitor 24, the return-light image G1 and the average fluorescence image G2 may be juxtaposed or may be superimposed. In addition, the return-light image G1 may be for the return-light image information in the G-buffer 25b or that in the B-buffer 25c.

In this case, with the fluorescence endoscope apparatus 1 according to this embodiment, the number S6 of integrated images for the fluorescence image is set by using the average gradation value S5 obtained by summing and averaging the gradation values of all pixels in the return-light image. Because the number S6 of integrated images is set so that the number is decreased with an increase in the average gradation value S5, it is possible to reduce the image blurring in the average fluorescence image information S3 generated by the average-image generating portion 29.

Specifically, when the average gradation value S5 of the return-light image is high, the illuminating portion 4 and the imaging subject A are close to each other or facing each other, and thus, the intensity of the excitation light radiated onto the imaging subject A is also high.

Therefore, when the average gradation value S5 of the return-light image is high, by setting the number S6 of integrated images to be small, it is possible to prevent the occurrence of image blurring in the average fluorescence image information S3 by preventing a large amount of fluorescence image information S2 having high gradation values and a good S/N ratio from being integrated.

On the other hand, when the average gradation value S5 of the return-light image is low, the distance between the illuminating portion 4 and the imaging subject A is large, and thus, the intensity of the excitation light radiated onto the imaging subject A is also low. Because of this, by setting the number S6 of integrated images to be large, it is possible to reduce noise by integrating a large amount of fluorescence image information S2 having low gradation values and a low S/N ratio. In this case, because the gradation values in the individual pieces of fluorescence image information S2 are low, it is less likely that image blurring remains in the average fluorescence image information S3 even if a large amount of fluorescence image information S2 is integrated.

Specifically, with the fluorescence endoscope apparatus 1 according to this embodiment, there is an advantage in that a clear average fluorescence image information S3 having low noise and low image blurring can be obtained when the average gradation value S5 of the return-light image is low as well as high.

Note that, when setting the number S6 of integrated images in this embodiment, the average gradation value S5 obtained by summing and averaging the gradation values of all pixels in the return-light image is extracted at the image-information extracting portion 26; however, it is preferable to extract a total contour length in which gradation values of adjacent pixels in the return-light image change by an amount exceeding a predetermined threshold. The contour can be extracted by, for example, estimating the gradient in two axial directions by calculating the magnitude of changes in pixel values, and so forth. By doing so, the edges of irregularities at the surface of the imaging subject A can be obtained as a continuous curve, making it possible to extract structural attributes of the image.

In other words, locations where the brightness of an image changes by an amount exceeding the predetermined threshold due to changes in the shape of the imaging subject A, the angle at which the illuminating portion 4 irradiates the imaging subject A, and so forth, are extracted in the form of a contour, and, when the total contour length is long, there are a large number of protrusions and depressions in the imaging subject A, which corresponds to when the illuminating portion 4 points in a direction along a body-cavity surface when the imaging subject A is a body cavity or the like. On the other hand, when the total contour length is short, there are a small number of protrusions and depressions in the imaging subject A, which corresponds to when the illuminating portion 4 points in a direction toward a body-cavity wall surface when the imaging subject A is a body cavity or the like.

Then, at the number-of-integrated-images setting portion 27, instead of using the function with which the number S6 of integrated images is decreased with an increase in the average gradation value 5, the number S6 of integrated images may be set by using a function with which the number S6 of integrated images is increased with an increase in the total contour length extracted by the image-information extracting portion 26.

By doing so, it is possible to achieve the same advantage as with the case in which the average gradation value S5 is used by means of the number S6 of integrated images determined by using the total contour length.

In addition, when setting the number S6 of integrated images in this embodiment, the average gradation value S5 obtained by summing and averaging the gradation values of all pixels in the return-light image is extracted at the image-information extracting portion 26; however, it is preferable to extract a gradation-value distribution (profile) along a straight line that horizontally runs across the return-light image. With the gradation-value distribution along the straight line that horizontally runs across the return-light image, conditions between the illuminating portion 4 and the imaging subject A can be determined from the shape of the distribution when, for example, the gradation-value intensity on the vertical axis and the positional information on the horizontal axis are represented.

The gradation values generally become the highest near the center of the return-light image when the illuminating portion 4 and the flat imaging subject A face each other. Therefore, when the gradation values are low near the center of the return-light image, the illuminating portion 4 points in a direction along a body-cavity surface when the imaging subject A is a body cavity or the like, and the return-light image becomes dark because the distance from the illuminating portion 4 to the imaging subject A is increased at the center.

On the other hand, when the gradation values are high near the center of the return-light image, the illuminating portion 4 points in the direction toward a body-cavity wall surface when the imaging subject A is a body cavity or the like, and the return-light image becomes bright because the distance from the illuminating portion 4 to the imaging subject A is decreased at the center.

Then, at the number-of-integrated-images setting portion 27, the number S6 of integrated images may be set by using a function with which the number S6 of integrated images is increased with a decrease in the gradation-value distribution near the center of the return-light image extracted by the image-information extracting portion 26.

Here, a single straight line may be used as the straight line that horizontally runs across the return-light image or a plurality of different straight lines may be used. By extracting an average value of the gradation-value distributions along a plurality of straight lines, the number S6 of integrated images can be set based on the average gradation-value distribution for a wider area in the image. In addition, the gradation-value distributions for individual pixel rows may be averaged for all pixel rows.

In addition, when setting the number S6 of integrated images in this embodiment, the average gradation value S5 obtained by summing and averaging the gradation values of all pixels in the return-light image is extracted at the image-information extracting portion 26; however, a total contour length in which the gradation values of the return-light image change discontinuously or a gradation-value distribution along a straight light that horizontally runs across the return-light image may additionally be extracted, after extracting the average gradation value S5, and the number S6 of integrated images may be set by the number-of-integrated-images setting portion 27 depending on whether the illuminating portion 4 points in the direction along the body-cavity surface or the illuminating portion 4 points in the direction toward the body-cavity wall surface.

In addition, in this embodiment, although an example function, such as the one shown in FIG. 2, is used when calculating the number S6 of integrated images for the fluorescence images, any other functions may be used instead of this, so long as it is a monotonically decreasing function. In addition, the number S6 of integrated images may be set by storing the function in the form of a calculation formula or by storing a map indicating the correspondence relationship between the number S6 of integrated images and the average gradation value S5.

In addition, in this embodiment, when extracting the image information of the return-light image at the image-information extracting portion 26, the image information may be extracted by using pixels whose gradation values are equal to or below a threshold. By doing so, it is not necessary to take saturated pixels into consideration, and it is possible to prevent the average gradation value S5 from becoming high.

In addition, in this embodiment, when determining the number S6 of integrated images for the fluorescence images by using the function at the number-of-integrated-images setting portion 27, the number S6 of integrated images may be adjusted by multiplying the gradient of the function by n (n is assumed to be a natural number).

Figure 5:
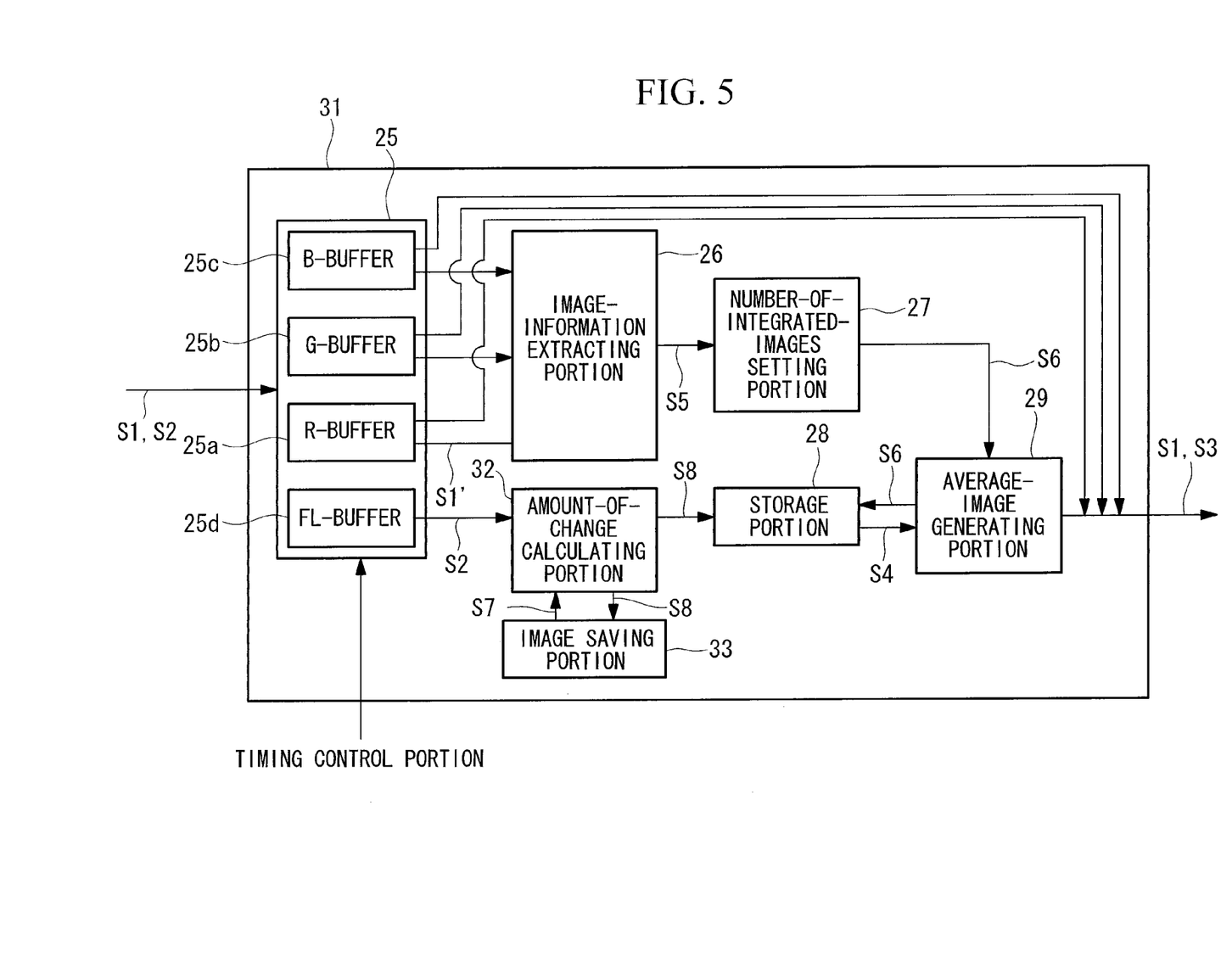
FIG. 5 is a diagram showing an image processing portion of a fluorescence endoscope apparatus according to a second embodiment of the present invention.

Next, a fluorescence endoscope apparatus according to a second embodiment of the present invention will be described below.

In describing this embodiment, the same reference signs are assigned to portions having common configurations with the fluorescence endoscope apparatus 1 according to the first embodiment described above, and descriptions thereof will be omitted. Note that, as shown in FIG. 5, the fluorescence endoscope apparatus according to this embodiment differs from the fluorescence endoscope apparatus 1 according to the first embodiment in terms of an image processing portion 31.

As shown in FIG. 5, an amount-of-change calculating portion 32 and an image saving portion 33 are provided between the FL-buffer 25*d* and the storage portion 28.

The amount-of-change calculating portion 32 outputs the most recent fluorescence image information S2 input from the FL-buffer 25*d* to the image saving portion 33, also obtains saved past fluorescence image information S7 from the image saving portion 33 to calculate the difference in the gradation values with respect to the most recent fluorescence image information S2, and, by extracting a weight coefficient from a table that is stored in advance, multiplies the most recent fluorescence image information S2 by the weight coefficient.

In addition, the amount-of-change calculating portion 32 is set so that the weight coefficient is decreased with an increase in the summed total of the differences in the gradation values between the saved past fluorescence image information S7 and the most recent fluorescence image information S2.

Specifically, because the imaging subject A has moved by a large amount when the differences in the gradation values are large for subtracted images, image blurring occurs when performing the integration. Accordingly, it is possible to reduce the image blurring by decreasing a contribution ratio in the average fluorescence image by decreasing the weight coefficient.

On the other hand, because the imaging subject A has not moved by a large amount when the differences in the gradation values are small for the subtracted images, it is possible to increase the clearness of the image and also to enhance the noise reduction effect by increasing the contribution ratio in the average fluorescence image by increasing the weight coefficient.

The storage portion 28 obtains fluorescence image information S8, which has been multiplied by the stored weight coefficient, in an amount corresponding to the number S6 of integrated images output by the number-of-integrated-images setting portion 27, and outputs the fluorescence image information S4 to the average-image generating portion 29 in an amount corresponding to the number S6 of integrated images.

The table stored in advance in the image saving portion 33 is obtained in advance based on the relationship between the difference in the gradation values of the subtracted images and the weight coefficient. Because the imaging subject A has moved by a larger amount when the differences in the subtracted images are larger, in order to reduce image blurring caused by having a large contribution ratio in the average fluorescence image, the weight coefficient is decreased with an increase in the differences in the subtracted images.

With the thus-configured fluorescence endoscope apparatus according to this embodiment, there is an advantage in that a clear average fluorescence image having low noise and low image blurring can be obtained when the imaging subject A has moved by a large amount as well as when the imaging subject A has not moved by a large amount.

Note that, in this embodiment, the saved past fluorescence image information S7 is obtained from the image saving portion 33, and the summed total of the differences in the gradation values with respect to the most recent fluorescence image information S2 is calculated; however, the difference between a total contour length of the past fluorescence image information S7 and a total contour length of the most recent fluorescence image information S2 may be calculated.

Specifically, because the imaging subject A has not moved by a large amount when the amount of movement between the contours of the subtracted images is small, it is possible to reduce noise by increasing the contribution ratio in the average fluorescence image by increasing the weight coefficient. On the other hand, because the imaging subject A has moved by a large amount when the amount of movement between the contours of the subtracted images is large, it is possible to reduce image blurring by decreasing the contribution ratio in the average fluorescence image by decreasing the weight coefficient.

In addition, with the amount-of-change calculating portion 32 in this embodiment, when the summed total of the gradation values of a subtracted image between the past fluorescence image information S7 and the most recent fluorescence image information S2 is equal to or below a threshold, the amount-of-change calculating portion 32 may calculate the amount of movement of the contours between the fluorescence images, and, by extracting a weight coefficient from the table stored in advance, the amount-of-change calculating portion 32 may multiply the most recent fluorescence image information by the weight coefficient. By doing so, the images in the case where the imaging subject has moved by a large amount can be excluded from the integration, and the average fluorescence image can be calculated with high precision.

In addition, in this embodiment, the fluorescence image may be output to the D/A converting portion without multiplying the fluorescence image by the weight coefficient when it is zero.

By doing so, when the imaging subject has moved by a large amount or the like, it is possible to prevent image blurring that occurs when integrating the average fluorescence images.

In addition, in this embodiment, when the average fluorescence image G2 is generated via the D/A converting portion 23 by using the average fluorescence image information S3 output from the average-image generating portion 29, the average fluorescence image information S3 may be adjusted at the average-image generating portion 29 so that the gradation values of the generated average fluorescence image G2 will be m (m is assumed to be a natural number). By doing so, the brightness of the generated average fluorescence image G2 is normalized, making high-precision observation possible.

In addition, although the above-described individual embodiments have been described in terms of examples in which the return-light image information S1' from the R-buffer 25*a* is used in the image-information extracting portion 26, it is not limited thereto, and return-light image information from other buffers may be used.

The following aspects of invention are derived from the embodiment and modifications thereof described above.

An aspect of the present invention is a fluorescence endoscope apparatus including an illuminating portion that radiates excitation light and illumination light onto an imaging subject; a fluorescence imaging portion that acquires a fluorescence image by capturing fluorescence emitted at the imaging subject due to the irradiation with the excitation light from the illuminating portion; a storage portion that stores the fluorescence image acquired by the fluorescence imaging portion; a return-light imaging portion that acquires a return-light image by capturing return light returning from the imaging subject due to the irradiation with the illumination light from the illuminating portion; an image-information extracting portion that extracts, from the return-light image acquired by the return-light imaging portion, image information that expresses the intensity of the illumination light radiated onto the imaging subject; a number-of-integrated-images setting portion that sets a number of integrated images so that the number is decreased with an increase in the intensity of the illumination light, based on the image information extracted by the image-information extracting portion; and an average-image generating portion that generates an average image by averaging the fluorescence images, stored in the storage portion, in a number corresponding to the number of integrated images set by the number-of-integrated-images setting portion.

With the aspect of the present invention, when the excitation light emitted from the illuminating portion is radiated onto the imaging subject, a fluorescent substance contained in the imaging subjects is excited to generate fluorescence, which is captured by the fluorescence imaging portion, and thus, fluorescence images are acquired. Then, the acquired fluorescence images are sequentially stored in the storage portion.

In addition, when the illumination light emitted from the illuminating portion is radiated onto the imaging subject, return light returning from the imaging subject is captured by the return-light imaging portion, and thus, return-light images are acquired. Then, from the acquired return-light images, image information that expresses the intensity of the illumination light radiated onto the imaging subject is extracted by the image-information extracting portion.

Because the excitation light and the illumination light are radiated onto the same imaging subject from the same illuminating portion, there is a correspondence between the intensity of the illumination light and the intensity of the excitation light radiated onto the imaging subject. In other words, when the intensity of the illumination light radiated onto the imaging subject is high, the intensity of the excitation light is also high, and when the intensity of the illumination light is low, the intensity of the excitation light is also low. Therefore, by extracting the image information that expresses the intensity of the illumination light radiated onto the imaging subject from the return-light images by means of the image-information extracting portion, it is possible to estimate the intensity of the excitation light that is radiated onto the imaging subject when the fluorescence images are acquired by the fluorescence imaging portion.

Then, the fluorescence images stored in the storage portion, in a number corresponding to the number of integrated images, which is set by the number-of-integrated-images setting portion in accordance with the extracted image information, are integrated and an average thereof is taken, thus generating an average image.

In this case, because the number of integrated images used when calculating the average image for the fluorescence images is decreased with an increase in the intensity of the illumination light, low-noise, bright fluorescence images are integrated using a small number of integrated images, making it possible to reduce the image blurring caused by using a large number of integrated images. On the other hand, because the number of integrated images is increased when the intensity of the illumination light is low, dark fluorescence images, with which the image blurring is less likely to become conspicuous even when a large number thereof are integrated, are integrated using a large number of integrated images, making it possible to satisfactorily reduce noise contained in the acquired average image.

In the above-described aspect, the image-information extracting portion may extract the image information in the form of an average gradation value for a plurality of pixels in the return-light image.

Because the distance between the illuminating portion and the imaging subject is large when the average gradation value for the plurality of pixels in the return-light image is low, the intensity of the excitation light radiated onto the imaging subject is also low. Because fluorescence images acquired in this case are high-noise, dark fluorescence images, even if the fluorescent substance exists in the imaging subject, a clear image can be obtained by enhancing the noise reduction effect by setting the number of integrated images to be large.

On the other hand, because the distance between the illuminating portion and the imaging subject is small when the average gradation value for the plurality of pixels in the return-light image is high, the intensity of the excitation light radiated onto the imaging subject is also high. Because fluorescence images acquired in this case are low-noise, bright fluorescence images if the fluorescent substance exists in the imaging subject, the image blurring can be reduced by setting the number of integrated images to be small, making it possible to cut down the processing and time required for computations.

In addition, in the above-described aspect, the image-information extracting portion may extract the image information in the form of a total contour length that represents locations where gradation values of adjacent pixels in the return-light image change by an amount exceeding a predetermined threshold.

The contour, which represents locations where the gradation values of the adjacent pixels in the return-light image change by an amount exceeding the predetermined threshold, indicates changes in the shape of the imaging subject, in particular, the protrusions and depressions thereof. When the total contour length is long, the illuminating portion points in a direction in which a larger number of protrusions and depressions in the imaging subject are visible (for example, a direction along a body-cavity surface when the imaging subject is a body cavity). Therefore, there are a large number of regions for which the distance from the illuminating portion is large in an area within the viewing field, and thus, the intensity of the excitation light radiated onto the imaging subject also becomes low. Because of this, fluorescence images become dark even if the fluorescent substance exists; therefore, the noise reduction effect can be increased by setting the number of integrated images to be large, making it possible to obtain a clear image.

On the other hand, when the total contour length is short, the illuminating portion points in a direction in which a smaller number of protrusions and depressions in the imaging subject are visible (for example, a direction toward a body-cavity wall surface when the imaging subject is a body cavity). Therefore, there is no region for which the distance from the illuminating portion is large in the area within the viewing field, and thus, the intensity of the excitation light radiated onto the imaging subject also becomes high. Because of this, low-noise, bright fluorescence images are obtained if the fluorescent substance exists; therefore, the image blurring can be reduced by setting the number of integrated images to be small. In addition, it is possible to cut down on the processing and time required for computations by decreasing the number of integrated images.

In addition, in the above-described aspect, the image-information extracting portion may extract the image information in the form of a gradation-value distribution along a straight line that horizontally runs across the return-light image.

In addition, in the above-described aspect, the image-information extracting portion may extract the image information by averaging gradation-value distributions along a plurality of straight lines that horizontally run across the return-light image.

The gradation values generally become the highest near the center of the return-light image when the illuminating portion and a flat imaging subject face each other. Therefore, when the gradation-value distribution is such that the gradation values are low near the center of the return-light image, the illuminating portion points toward an imaging subject whose center is far therefrom, that is, in the direction along, for example, a body-cavity surface when the imaging subject is a body cavity, and, because the return-light image becomes dark due to the large distance from the illuminating portion to the imaging subject, the intensity of the excitation light radiated onto the imaging subject also becomes low. In this case, the noise reduction effect can be increased by setting the number of integrated images to be large, making it possible to obtain a clear image.

On the other hand, when the gradation-value distribution is such that the gradation values are high near the center of the return-light image, the illuminating portion points in a direction toward, for example, a body-cavity wall surface when the imaging subject is a body cavity, and because the return-light image becomes bright due to the small distance from the illuminating portion to the imaging subject, the intensity of the excitation light radiated onto the imaging subject also becomes high. In this case, the image blurring can be reduced by setting the number of integrated images to be small. In addition, it is possible to cut down on the processing and time required for computations by decreasing the number of integrated images.

In this case, by averaging gradation-value distributions along the plurality of straight lines, the direction of the illuminating portion can be judged more accurately based on an average gradation value distribution for a larger area in the return-light image.

In addition, in the above-described aspect, an amount-of-change calculating portion may be included, which calculates an amount of change between a first fluorescence image acquired by the fluorescence imaging portion and a second fluorescence image acquired before the first fluorescence image, and the storage portion may store the first fluorescence image by multiplying the image by a weight coefficient that is increased with a decrease in the amount of change calculated by the amount-of-change calculating portion.

By doing so, when the amount of change relative to the past fluorescence images is small, the noise reduction effect can be enhanced by increasing a contribution ratio in an average image by multiplying the acquired fluorescence images by a large weight coefficient.

On the other hand, when the amount of change is large, the image blurring can be reduced by decreasing the contribution ratio in the average image by multiplying the acquired fluorescence images by a small weight coefficient.

In addition, in the above-described aspect, the amount-of-change calculating portion may calculate the amount of change in the form of a summed total of gradation values of a subtracted image between the first fluorescence image and the second fluorescence image.

When the summed total of differences between the individual gradation values of the same pixels in the two fluorescence images is small, the distance between the illuminating portion and the imaging subject has not changed by a large amount. Therefore, it is possible to obtain a clear image and also to enhance the noise reduction effect by increasing the contribution ratio in the average image by increasing the weight coefficient.

On the other hand, when the summed total of the differences between the gradation values for the individual pixels at the same positions in the two fluorescence images is large, the distance between the illuminating portion and the imaging subject has changed by a large amount. Therefore, the image blurring can be reduced by decreasing the contribution ratio in the average image by decreasing the weight coefficient.

In addition, in the above-described aspect, the amount-of-change calculating portion may calculate the amount of change in the form of a difference between a total contour length of the first fluorescence image and a total contour length of the second fluorescence image.

When the difference between the total contour lengths in the two fluorescence images is small, the imaging subject has not moved by a large amount, and thus, the change in conditions between the fluorescence images is small. Therefore, the noise reduction effect can be enhanced by increasing the contribution ratio in the average image by increasing the weight coefficient.

On the other hand, when the difference between the total contour lengths in the two fluorescence images is large, the imaging subject has moved by a large amount, and thus, the change in conditions between the fluorescence images is large. Therefore, the image blurring can be reduced by decreasing the contribution ratio in the average image by decreasing the weight coefficient.

In addition, in the above-described aspect, the amount-of-change calculating portion may calculate the amount of change in the form of a difference between the contour of the first fluorescence image and the contour of the second fluorescence image, when the summed total of the gradation values of the subtracted image between the first fluorescence image and the second fluorescence image is equal to or below a threshold.

When the summed total of the gradation values of the subtracted image between the first fluorescence image and the second fluorescence image is equal to or below the threshold, the imaging subject has not moved by a large amount between the two fluorescence images described above. Furthermore, by calculating the weight coefficient based on the amount of movement between the contours of the two fluorescence images in this state, conditions between the images can be judged with high precision, making it possible to calculate a more appropriate weight coefficient.

ADVANTAGEOUS EFFECTS OF INVENTION

The present invention affords an advantage in that the occurrence of image blurring in a fluorescence image can be prevented while reducing a noise level in the fluorescence image.

REFERENCE SIGNS LIST

A imaging subject
S5 image information (average gradation value)
1 fluoroscopy apparatus
3 light source (illuminating portion)
4 illuminating unit (illuminating portion)
18 imaging device (return-light imaging portion, fluorescence imaging portion)
26 image-information extracting portion
27 number-of-integrated-images setting portion
28 storage portion
29 average-image generating portion
32 amount-of-change calculating portion

The invention claimed is:
1. A fluorescence endoscope apparatus comprising:
an illuminating portion that radiates excitation light and illumination light onto an imaging subject;
a fluorescence imaging portion that acquires a fluorescence image by capturing fluorescence emitted at the imaging subject due to the irradiation with the excitation light from the illuminating portion;

a storage portion that stores the fluorescence image acquired by the fluorescence imaging portion;

a return-light imaging portion that acquires a return-light image by capturing return light returning from the imaging subject due to the irradiation with the illumination light from the illuminating portion;

an image-information extracting portion that extracts, from the return-light image acquired by the return-light imaging portion, image information that expresses the intensity of the illumination light radiated onto the imaging subject;

a number-of-integrated-images setting portion that sets a number of integrated images so that the number is decreased with an increase in the intensity of the illumination light, based on the image information extracted by the image-information extracting portion; and an average-image generating portion that generates an average image by averaging the fluorescence images, stored in the storage portion, in a number corresponding to the number of integrated images set by the number-of-integrated-images setting portion.

2. A fluorescence endoscope apparatus according to claim 1, wherein the image-information extracting portion extracts the image information in the form of an average gradation value for a plurality of pixels in the return-light image.

3. A fluorescence endoscope apparatus according to claim 1, wherein the image-information extracting portion extracts the image information in the form of a total contour length that represents locations where gradation values of adjacent pixels in the return-light image change by an amount exceeding a predetermined threshold.

4. A fluorescence endoscope apparatus according to claim 1, wherein the image-information extracting portion extracts the image information in the form of a gradation-value distribution along a straight line that horizontally runs across the return-light image.

5. A fluorescence endoscope apparatus according to claim 1, wherein the image-information extracting portion extracts the image information by averaging gradation-value distributions along a plurality of straight lines that horizontally run across the return-light image.

6. A fluorescence endoscope apparatus according to claim 1, further comprising:

an amount-of-change calculating portion that calculates an amount of change between a first fluorescence image acquired by the fluorescence imaging portion and a second fluorescence image acquired before the first fluorescence image, wherein the storage portion stores the first fluorescence image by multiplying the image by a weight coefficient that is increased with a decrease in the amount of change calculated by the amount-of-change calculating portion.

7. A fluorescence endoscope apparatus according to claim 6, wherein the amount-of-change calculating portion calculates the amount of change in the form of a summed total of gradation values of a subtracted image between the first fluorescence image and the second fluorescence image.

8. A fluorescence endoscope apparatus according to claim 6, wherein the amount-of-change calculating portion calculates the amount of change in the form of a difference between a total contour length of the first fluorescence image and a total contour length of the second fluorescence image.

9. A fluorescence endoscope apparatus according to claim 6, wherein the amount-of-change calculating portion calculates the amount of change in the form of a difference between the contour of the first fluorescence image and the contour of the second fluorescence image, when the summed total of the gradation values of the subtracted image between the first fluorescence image and the second fluorescence image is equal to or below a threshold.

* * * * *